United States Patent [19]

Effland et al.

[11] Patent Number: 4,992,448
[45] Date of Patent: Feb. 12, 1991

[54] BENZOCYCLOALKYLAMINOPYRIDINA-MINES AND RELATED COMPOUNDS AS TOPICAL ANTIINFLAMMATORY AGENTS FOR THE TREATMENT OF SKIN DISORDERS

[75] Inventors: Richard C. Effland; Joseph T. Klein, both of Bridgewater; Gordon E. Olsen, Somerset; Larry Davis, Sergeantsville, all of N.J.

[73] Assignee: Hoechst-Roussel Pharmaceuticals Inc., Somerville, N.J.

[21] Appl. No.: 425,712

[22] Filed: Oct. 24, 1989

[51] Int. Cl.$^5$ .................. A61K 31/47; C07D 401/04
[52] U.S. Cl. ........................ 514/207; 514/213; 514/314; 514/339; 540/593; 546/144; 546/159; 546/272; 546/273
[58] Field of Search ............ 546/144, 159, 272, 273; 540/593; 514/307, 213, 314, 339

[56] References Cited

U.S. PATENT DOCUMENTS

| | | | |
|---|---|---|---|
| 3,118,884 | 1/1964 | Clarke | 260/243 |
| 3,495,969 | 2/1970 | Driscoll | 71/94 |
| 3,576,616 | 4/1971 | Nowotny | 71/94 |
| 3,721,676 | 3/1973 | Witzer et al. | 260/296 |
| 4,042,697 | 8/1977 | Garside et al. | 546/144 |
| 4,190,660 | 2/1980 | Siu | 546/144 |
| 4,609,733 | 9/1986 | Boyer et al. | 546/273 |

FOREIGN PATENT DOCUMENTS

| | | |
|---|---|---|
| A69885/87 | 9/1987 | Australia . |
| 0110405 | 6/1984 | European Pat. Off. . |
| 2073736 | 10/1981 | United Kingdom . |

OTHER PUBLICATIONS

Brewster, et al., "J. Het. Chem.", vol. 15, 1975, pp. 1497–1499.
Butler, et al., "J. Med. Chem.", vol. 24, 1981, pp. 346–350.
Ito, et al., "Chem. Parm. Bull.", vol. 26, No. 5, 1978, pp. 1375–1388.

Primary Examiner—Richard L. Raymond
Assistant Examiner—James H. Turnipseed
Attorney, Agent, or Firm—Tatsuya Ikeda

[57] ABSTRACT

There are described compounds of the formula,

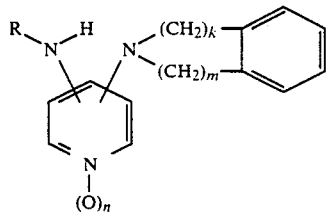

where
R is hydrogen, loweralkyl, arylloweralkyl or loweralkylcarbonyl;
k is 0 or 1;
m is 1,2 or 3;
k+m is 2 or 3; and
n is 0 or 1;
which compounds are useful as topical antiinflammatory agents for the treatment of various dermatoses.

14 Claims, No Drawings

BENZOCYCLOALKYLAMINOPYRIDINAMINES AND RELATED COMPOUNDS AS TOPICAL ANTIINFLAMMATORY AGENTS FOR THE TREATMENT OF SKIN DISORDERS

The present invention relates to compounds of Formula I, (I)

where
R is hydrogen, loweralkyl, arylloweralkyl or loweralkylcarbonyl;
k is 0 or 1;
m is 1, 2 or 3;
k+m is 2 or 3; and
n is 0 or 1;
which compounds are useful as topical antinflammatory agents for the treatment of various dermatoses including, for example, exogenous dermatitides (e.g. sunburn, photoallrtgic drmatitis, urticaria, contact dermatitis, allergic dermatitis), endogenous dermatitides (e.g. atopic dermatitis, seborrheic dermatitis, nummular dermatitis), dermatitides of unknown etiology (e.g. generalized exfoliative dermatitis), and other cutaneous disorders with an inflammatory component (e.g. psoriasis).

Also included within the scope of this invention are compounds of Formula II where k, m and n are as defined above, which are useful for the same dermatological applications as mentioned above and also as direct precursors of the compounds of Formula I.

(II)

Unless otherwise stated or indicated, the following definitions shall apply throughout the specification and the appended claims.

The term loweralkyl shall mean a straight or branched alkyl group having from 1 to 6 carbon atoms. Examples of said loweralkyl include methyl, ethyl, n-propyl, iso-propyl, n-butyl, iso-butyl, sec-butyl, t-butyl and straight- and branched-chain pentyl and hexyl.

The term halogen shall means fluorine, chlorine, bromine or iodine.

The term aryl shall means a phenyl group optionally mono-substituted with a loweralkyl, loweralkoxy, halogen or trifluoromethyl group.

Throughout the specification and the appended claims, a given chemical formula or name shall encompass all stereo, optical, geometrical and tautomeric isomers where such isomers exist.

The compounds of this invention are prepared by utilizing one or more of the synthetic steps described below.

Throughout the description of the synthetic steps, the notations R, k, m, and n shall have the respective meaning given above unless otherwise stated or indicated, and other notations shall have the respective meanings defined in their first appearances unless otherwise stated or indicated.

STEP A

A compound of Formula II where Hal is F or Cl, preferably F, is allowed to react with a compound of Formula IV to afford a compound of Formula II.

(III)  (IV)

this reaction is typically conducted in a suitable solvent such as ethanol, dimethylformamide, diemthylsulfoxide or N-methylpyrrolidone at a temperature of about 0 to 150° C.

3-Fluoro-4-nitropyridine-1-oxide, which belongs to the group of compounds of Formula III, is disclosed in Talik and Talik, Roczniki Chemii, Volume 38, 777 (1964). 4-chloro-3-nitropyridine, which also belongs to the group of compounds of Formula III, is disclosed in Talik and Talik, Roczniki Chemii, Volume 43, 923 (1969).

STEP B

A compound of Formula IIa is selectively hydrogenated to afford a compound of Formula V.

(IIa)

(V)

This selective hydrogenation is typically conducted with the aid of a suitable catalyst such as Pd/C or PtO$_2$ and a suitable medium such as ethanol at a temperature of about 20 to 100° C.

STEP C

Compound IIa is catalytically hydrogenated in a manner similar to the one described in STEP B above, except that a longer reaction period or higher reaction temperature is preferably employed, to afford a compound of Formula VI.

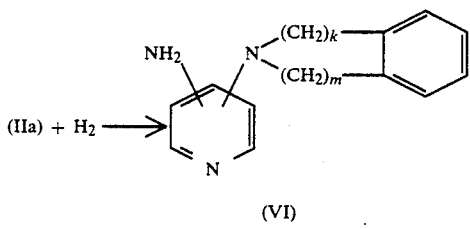

(VI)

Instead of using compounds IIa in the above reaction, one can also use compound V and conduct the hydrogenation is substantially the same manner as described above to obtain compound VI.

STEP D

A compound of Formula VII obtained from STEP B or C is allowed to react with a compound of the formula, R-Hal, where R is loweralkyl, arylloweralkyl or loweralkylcarbonyl and Hal is bromine or chlorine, in a routine manner known to the art to afford a compound of Formula I.

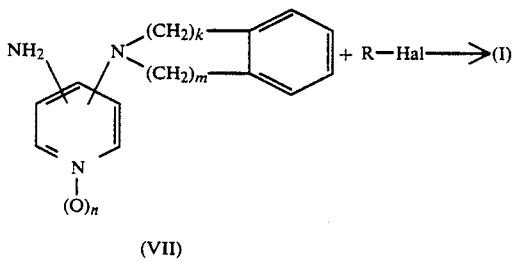

(VII)

Compounds of Formula I and Formula II according to this invention are useful as topical agents for the treatment of various skin disorders such as those mentioned earlier. The dermatological activates of the compounds of this invention were ascertained with reference to the following methods.

DERMATOLOGICAL TEST METHODS

Phospholipase $A_2$-induced Paw Edema (PIPE) $A_2$-induced paw edema in male Wistar rats (100–125 g) was measured. $PLA_2$ (3 units/paw) alone or with 0.1 M of the test compound was injected in the subplantar region of the rat left hind paw. Immediately subsequent to the injection and at two hours post administration the paw was immersed in a mercury bath, and paw displacement was measured on a recorder via a transducer. (Standard: hydrocortisone $ED_{50}=0.46$ $M$). See Giessler, A. J. et. al., *Agents and Actions*, Vol. 10, Trends in Inflammation Research (1981), p. 195.

In Vitro Phospholipase $A_2$ Assay ($PLA_2$)

The ability of a compound to modulate $PLA_2$ activity (clevage of $^{14}$-dipalmitoyl phosphotidylcholine at the 2-position to $^{14}C$-palmitic acid) was quantitated in this assay. The reaction mixture contained Tris buffer (25 mM), pH 8.0, calcium chloride (2.0 mM), bovine serum albumin (0.5 mg), dipalmitoyl phosphotidycholine ($8\times10^{-5}$M), ($^{14}$C-palmitoyl)dipalmitoyl Phosphotidylcholine ($6\times10^3$ cpm), porcine pancreatic $PLA_2$ (3.2 units) and the test compound. The reaction was run at 37° C. in a shaking incubator. The reaction was quenched and an internal standard was added in order to determine sample recovery. The samples were loaded onto $D_{18}$ columns, eluted with ethanol, and the radioactivity was then measured. (Standard: quinacrine $IC_{50}-3.5\times10^{-4}$M). See Feyen, J. H. M. et. al., *Journal of Chromatography* 259 (1983), pp. 338–340.

TPA-Induced Ear Edema (TPAEE)

The purpose of this assay was to determine the ability of a topically-applied compound to prevent ear edema induced by topical application of TPA (phorbol 12/myristate acetate). Female Swiss WEbster mice topically received TPA (10µg/ear) on the right ear and vehicle on the left ear. The test compound (10µg/ear) was applied to both ears. After five hours, the animals were sacrificed and an ear punch (4 mm) was taken from each ear. The difference in right and left ear punch weights for each animal was determined to uses activity. (Standard: hydrocortisone $ED_{50}=47/µg/ear$). See Yound, J. M. et. al., *J. Invest. Dermatol.*, 80 (1983), pp. 48–52.

Dermatological activities for some of the compounds of this invention are presented in Table 1.

TABLE 1

| Compound | PIPE* (0.1 M) | $PLA_2$* (0.01 M) | TPAEE (10 µg) |
|---|---|---|---|
| 1-(4-Amino-3-pyridinyl)-2,3-dihydro-1H-indole | −33% | −85% | −35% |
| 1-(3-Amino-4-pyridinyl)-2,3-dihydro-1H-indole | −34% | −42% | −74% |
| 2-(4-Amino-3-pyridinyl)-1,2,3,4-tetrahydroisoquinoline, N-oxide | −42% | −59% | −45% |

*difference in edema vs. control

Examples of the compounds of this invention include:
1-(4-Amino-3-pyridinyl)-2,3-dihydro-01H-indole;
1-(3-Amino-4-pyridinyl)-2,3-dihydro-1H-indole;'
1-(4-Amino-3-pyridinyl)-1,2,3,4-tetrahydroquinoline;
2-(4-Amino-3-pyridinyl)-1,2,3,4-tetrahydroisoquinoline, N-oxide;
N-[3-(2,3-Dihydro-1H-indol-1-yl)pyridin-4-yl]acetamine;
2,3-Dihydro-1-(4-nitro-3-pyridinyl)-1H-indole,N-oxide;
2,3-Dihydro-1-(4-nitro-3-pyridinyl)-1H-indole;
1-(4-Nitro-3-pyridinyl)-1,2,3,4-tetrahydroquinoline, N-oxide;
2-(4-Nitro-3-pyridinyl)-1,2,3,4-tetrahydroisoquinoline, N-oxide;
1-(3-Methylamino-4-pyridinyl)-2,3-dihydro-1H-indole;
1-(3-Benzylamino-4-pyridinyl)-2,3-dihydro-1H-indole;
2-(4-Amino-3-pyridinyl)-1,2,3,4-tetrahydroquinoline;
1-(4-Propylamino-3-pyridinyl)-1,2,3,4-tetrahydroquinoline; and
2-[3-(2-Phenylethyl)amino-4-pyridinyl]-1,2,3,4-tetrahydroisoquinoline, N-oxide;

The following examples are presented in order to illustrate this invention:

EXAMPLE 1

2,3-Dihydro-1-(4-nitro-3-pyridinyl)-1H-indole, N-oxide

A solution of 3-fluoro-4-nitropyridein-N-oxide[1] (5 g) and indoline (4 g) in 100 ml ethanol was stirred for one hour at reflux and thereafter cooled and concentrated. The residue was purified by flash chromatography (silca, ethyl actate) to give 8 g solid, m.p. 168–170°. Four grams were recrystallized from ethanol to give 3 g needles, m.p. 170–172°.

[1]Talik and Talik; Roczniki Cheii, 38, 777 (1964)

| Analysis | | | |
|---|---|---|---|
| Calculated for $C_{13}H_{11}N_3O_3$ | 60.69% C | 4.31% H | 16.34% N |
| Found | 60.55% C | 4.22% H | 16.11% N |

EXAMPLE 2

2,3-Dihydro-1-(3-nitro-4-pyridinyl)-1H-indole

To 50 ml ethanol were added 4-chloro-3-nitropyridine (10 g) and triethylamine (8 ml) followed by a solution of indoline (7.0 ml) in 50 ml ethanol.

After stirring at ambient temperature for one hour, a precipitate began forming, and stirring was continued for five hours. The mixture was poured into 500 ml water, the pH was adjusted to 10 with a $Na_2CO_3$ solution, and the resultant precipitate was collected, washed with ether and dried at 50° C. overnight in a vacuum oven to give 8.2 g solid, d @ 156–158° C. A 3.0 g sample of this material was recrystallized from ethanol/ether (1:1) to give a solid, 2.3 g, m.p. 159–160° C.

| Analysis | | | |
|---|---|---|---|
| Calculated for $C_{13}H_{11}N_3O_2$ | 64.72% C | 4.60% H | 17.42% N |
| Found | 64.76% C | 4.57% H | 17.37% N |

EXAMPLE 3

1-(4-Nitro-3-pyridinyl)-1,2,3,4-tetrahydroquinoline, N-oxide

To 100 ml of ethanol were added 3-fluoro-4-nitropyridine-N-oxide (7.0 g) and 1,2,3,4-tetrahydroquinoline (6.89 ml) and this mixture was heated to 70° C. and stirred for 13 hours. The reaction mixture was then cooled, poured into water and extracted with ethyl acetate. The organic layer was washed with water and dried (saturated NaCl, anhy. $MgSO_4$).

After filtration, the solvent was evaporated to yield a solid (12.0 g), which was eluted with 10% ethyl acetate/dichlorometahne (DCM) and then with ethyl acetate on a silica gel column via HPLC. The desired fractions were concentrated to yield a solid (3.45 g). A 1.1 g sample was recrystallized from methanol to yield a solid, 0.6 g, m.p. 171–173° C.

| Analysis | | | |
|---|---|---|---|
| Calculated for $C_{14}H_{13}N_3O_3$ | 61.98% C | 4.83% H | 15.49% N |
| Found | 61.80% C | 4.80% H | 15.42% N |

EXAMPLE 4

2-(4-Nitro-3-pyridinyl)-1,2,3,4-tetrahydroisoquinoline, N-oxide

To 100 ml of ethanol were added 3-fluoro-4-nitropyridine-N-oxide (7.0 g) and 1,2,3,4-tetrahydroisoquiniline (6.38 g) and this mixture was heated to 60° C. and stirred for two hours. Filtration of the mixture afforded a solid (11.2 g). Recrystallization of a 3.0 g portion of this material yielded a solid, 2.2 g, m.p. 165–167° C.

| Analysis | | | |
|---|---|---|---|
| Calculated for $C_{14}H_{13}N_3O_3$ | 61.98% C | 4.83% H | 15.49% N |
| Found | 62.14% C | 4.91% H | 15.54% N |

EXAMPLE 5

1-(4-Amino-3-pyridinyl)-2,3-dihydro-1H-indole

A solution of 2,3-dihydro-1-(4-nitro-3-pyridinyl)-1H-indole, N-oxide (4.5 g) in 250 ml ethanol containing 0.5 g platinum oxide was hydrogenated at 50 psi (pounds per square inch) for five hours and thereafter filtered and concentrated to an oil. This oil was purified by flash chromatography (silica, 10% methanol in dichloromethane) to give 4 g oil. This oil was converted to the hydrochloride salt and decrystallized twice from ethanol/ether to give 3 g crystals, d 274°.

| Analysis | | | |
|---|---|---|---|
| Calculated for $C_{13}H_{13}N_3 \cdot HCl$ | 63.03% C | 5.70% H | 16.97% N |
| Found | 62.96% C | 5.64% H | 16.81% N |

EXAMPLE 6

1-(3-Amino-4-pyridinyl)-2,3-dihydro-1H-indole

In a 500 ml Parr hydrogenation bottle was suspended 1.0 g of 5% Pd/C in 25 ml ethanol, followed by a suspension of 2,3-dihydro-1-(3-nitro-4-pyridinyl)-1H-indole (4.7 g) in 125 ml ethanol. After shaking at 50 psi $H_2$ at ambient temperature for five hours the mixture was filtered and the filtrate concentrated to an oil (4.2 g). This oil was eluted on a silica gel column with ethyl acetate via HPLC and the desired fraction were combined and concentrated to give a solid, 4.0 g, m.p. 89–9° C. This material was recrystallized from ether/hexanes (4:1) to give solid, 2.9 g, m.p. 90–92° C.

| Analysis | | | |
|---|---|---|---|
| Calculated for $C_{13}H_{13}N_3$ | 73.91% C | 6.20% H | 19.89% N |
| Found | 74.08% C | 6.30% H | 19.94% N |

EXAMPLE 7

1-(4-Amino-3-pyridinyl)-1,2,3,4-tetrahydroquinoline hydrochloride

To a slurry of $PtO_2$ (0.3 g) in 10 ml of ethanol was added 1-(4-nitro-3-pyridinyl)-1,2,3,4-tetrahydroquinoline, N-oxide (2.5 g) in 240 ml of ethanol and this was hydrogenated with a Parr apparatus at room temperature for 48 hours. The mixture was then filtered and the filtrate concentrated to yield an oil (2.5 g), which was eluted with 10% methanol/DCM on a silica gel column via HPLC. The desired fractions were concentrated to yield an oil (1.5 g). This material was converted to the HCl salt with ethereal HCl and the resulting solid (1.45 g) was recrystallized from methanol/ether (1:5) to yield a solid, 0.8 g, m.p.>270° C.

| Analysis | | | |
|---|---|---|---|
| Calculated for $C_{14}H_{15}N_3\cdot HCl$ | 64.24% C | 6.16% H | 16.05% N |
| Found | 64.12% C | 6.10% H | 15.85% N |

EXAMPLE 8

2-(4-Amino-3-pyridinyl)-1,2,3,4-tetrahydroisoquinoline-N-oxide

To a slurry of $PtO_2$ (0.3 g) in 10 ml of ethanol was added 2-(4-nitro-3-pyridinyl)-1,2,3,4-tetrahydroisoquinolein, N-oxide (5.0 g) in 240 ml of ethanol and this was hydrogenated with a Parr apparatus at room temperature for 24 hours. The mixture was filtered and the filtrate concentrated to yield an oil (5.1 g), which was eluted with 20% methanol/DCM on a silica gel column via HPLC. The desired fractions were concentrated to a solid (2.0 g), m.p. 216–219° C. (decomp). This solid was recrystallized from acetonitirile to yield a solid, 1.0 g, m.p. 217–219° C.

| Analysis | | | |
|---|---|---|---|
| Calculated for $C_{14}H_{15}N_3O$ | 69.69% C | 6.27% H | 17.42% N |
| Found | 69.52% C | 6.27% H | 17.39% N |

EXAMPLE 9

N-[3-2,3-dihydro-1H-indol-1-yl)pyridin-4-yl]acetamide maleate

A solution of 1-(4-amino-3-pyridinyl)-2,3-dihydro-1H-indole (5 g) in 25 ml acetic anhydride was stirred for one hour at ambient temperature and thereafter concentrated, stirred with water, gasified with sodium carbonate and extracted with ethyl acetate. The organic extract was washed with water and saturated sodium chloride solution, dried (anhy. MgSO4) filtered and concentrated to 7 g oil. This oil was purified by flash chromatography (silica, 20% ethyl acetate in dichloromethane) to give 5 g solid, m.p. 123–125°. This solid was converted to the maleate salt in methanol/ether to give 5.6 g crystals, d 158–160°. A 2.5 g sample was recrystallized from methanol/ether to give 2.2 g crystals d 160–161°.

| Analysis | | | |
|---|---|---|---|
| Calculated for $C_{15}H_{15}N_3O\cdot C_4H_4O_4$ | 61.78% C | 5.18% H | 11.38% N |
| Found | 61.60% C | 5.11% H | 11.39% N |

We claim:
1. A compound having the formula,

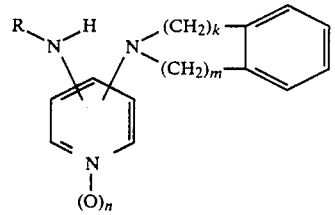

where
R is hydrogen, loweralkyl, arylloweralkyl or loweralkylcarbonyl;
k is 0 or 1;
m is 1, 2 or 3;
k+m is 2 or 3; and
n is 0 or 1;
or a pharmaceutically acceptable acid salt thereof.

2. The compound as defined in claim 1, where R is hydrogen or loweralkylcarbonyl.

3. The compound as defined in claim 1, which is 1-(4-amino-3-pyridinyl)-2,3-dihydro-1H-indole.

4. The compound as defined in claim 1, which is 1-(3-amino-4-pyridinyl)-2,3-dihydro-1H-indole.

5. The compound as defined in claim 1, which is 1-(4-amino-3-pyridinyl)-1,2,3,4-tetrahydroquinoline.

6. The compound as defined in claim 1, which is 2-(4-amino-3-pyridinyl)-1,2,3,4-tetrahydroisoquinoline, N-oxide.

7. The compound as defined in claim 1, which is N-[3-(2,3-dihydro-1H-indol-1-yl)pyridin-4-yl]acetamine.

8. The compound as defined in claim 1, which is 1-(3-methylamino-4-pyridinyl)-2,3-dihydro-1H-indole.

9. The compound as defined in claim 1, which is 1-(3-benzylamino-4-pyridinyl)-2,3-dihydro-1H-indole.

10. The compound as defined in claim 1, which is 2-(4-amino-3-pyridinyl)-1,2,3,4-tetrahydroisoquinoline.

11. The compound as defined in claim 1, which is 1-(4-propylamino-3-pyridinyl)-1,2,3,4-tetrahydroquinoline.

12. The compound as defined in claim 1, which is 2-[3-(2-phenylethyl)amino-4-pyridinyl]-1,2,3,4-tetrahydroquinoline, N-oxide.

13. A dermatological composition which comprises a compound as defined in claim 1 in an amount effective for treating a skin disorder, and a suitable carrier therefor.

14. A method of treating a patient in need of relief from a skin disorder which comprises administering to such a patient an effective amount of a compound as defined in claim 1.

* * * * *